United States Patent
Wang et al.

(10) Patent No.: US 12,130,596 B2
(45) Date of Patent: Oct. 29, 2024

(54) CONTROLLING METHOD FOR MONITORING PHYSIOLOGICAL CONDITION OF FIRST USER AND RELATED PRODUCTS

(71) Applicant: Telesair, Inc., Irvine, CA (US)

(72) Inventors: Qing Wang, Palo Alto, CA (US); Yong Liu, Orange, CA (US); Dongping Lin, Las Vegas, NV (US)

(73) Assignee: TELESAIR, INC., Irvine, CA (US)

( * ) Notice: Subject to any disclaimer, the term of this patent is extended or adjusted under 35 U.S.C. 154(b) by 0 days.

(21) Appl. No.: 18/076,577

(22) Filed: Dec. 7, 2022

(65) Prior Publication Data
US 2024/0192644 A1    Jun. 13, 2024

(51) Int. Cl.
| | |
|---|---|
| G05B 13/02 | (2006.01) |
| A61B 5/00 | (2006.01) |
| A61B 5/08 | (2006.01) |
| A61B 5/1455 | (2006.01) |
| G16H 10/60 | (2018.01) |
| G16H 50/30 | (2018.01) |
| H04N 7/18 | (2006.01) |

(52) U.S. Cl.
CPC ........ G05B 13/0265 (2013.01); A61B 5/0077 (2013.01); A61B 5/0816 (2013.01); A61B 5/14551 (2013.01); A61B 5/7221 (2013.01); A61B 5/743 (2013.01); A61B 5/746 (2013.01); G16H 10/60 (2018.01); G16H 50/30 (2018.01); H04N 7/183 (2013.01); A61B 2562/0204 (2013.01)

(58) Field of Classification Search
CPC . A61B 5/0077; A61B 5/0816; A61B 5/14551; A61B 5/7221; A61B 5/743; A61B 5/746; A61B 2562/0204; G05B 13/0265
See application file for complete search history.

(56) References Cited

U.S. PATENT DOCUMENTS

| 4,121,583 A | 10/1978 | Chen |
|---|---|---|
| 4,809,706 A | 3/1989 | Watson et al. |

(Continued)

FOREIGN PATENT DOCUMENTS

| CN | 204910621 U | 12/2015 |
|---|---|---|
| CN | 110051989 A | 7/2019 |
| WO | 2016022974 A1 | 2/2016 |

OTHER PUBLICATIONS

Non-Final Office Action dated Mar. 9, 2023, corresponding to co-pending related U.S. Appl. No. 18/076,610, 26 pages.

(Continued)

*Primary Examiner* — Lynsey C Eiseman
*Assistant Examiner* — Amanda L Steinberg
(74) *Attorney, Agent, or Firm* — Maier & Maier, PLLC

(57) ABSTRACT

A controlling method for monitoring a physiological condition of a first user. The method includes: obtaining first sensing data of the first user reported by at least one first sensing device; determining the physiological condition of the first user based on a result derived from the first sensing data and a reference range corresponding to the first sensing data; and upon determining that the physiological condition of the first user is abnormal, sending a control instruction to a second sensing device to switch the second sensing device from the first state to the second state.

20 Claims, 6 Drawing Sheets

(56) References Cited

U.S. PATENT DOCUMENTS

| | | | |
|---|---|---|---|
| 5,207,623 A | 5/1993 | Tkatchouk et al. | |
| 5,571,075 A | 11/1996 | Bullard | |
| 5,984,873 A | 11/1999 | Crumb et al. | |
| 6,131,569 A | 10/2000 | Schuster | |
| 11,468,988 B1 | 10/2022 | Wang et al. | |
| 2002/0035927 A1 | 3/2002 | Kutt et al. | |
| 2004/0006926 A1 | 1/2004 | Neeley et al. | |
| 2005/0059530 A1 | 3/2005 | Chang | |
| 2007/0023041 A1 | 2/2007 | Wang | |
| 2008/0132383 A1 | 6/2008 | Einav et al. | |
| 2008/0236582 A1 | 10/2008 | Tehrani | |
| 2008/0295839 A1 | 12/2008 | Habashi | |
| 2011/0120470 A1 | 5/2011 | Bowerbank | |
| 2011/0146687 A1 | 6/2011 | Fukushima | |
| 2012/0116179 A1* | 5/2012 | Drew | A61B 5/318 600/300 |
| 2012/0315614 A1 | 12/2012 | Krauza | |
| 2013/0160767 A1 | 6/2013 | Abella | |
| 2014/0000609 A1 | 1/2014 | Steinhauer et al. | |
| 2014/0235959 A1 | 8/2014 | Jafari et al. | |
| 2015/0224270 A1 | 8/2015 | Frandson | |
| 2015/0231443 A1 | 8/2015 | Halliday | |
| 2015/0231447 A1 | 8/2015 | Hsu | |
| 2015/0258560 A1 | 9/2015 | Ashby et al. | |
| 2015/0327804 A1 | 11/2015 | Lefever et al. | |
| 2015/0358790 A1* | 12/2015 | Nasserbakht | G06F 21/32 726/19 |
| 2016/0038071 A1 | 2/2016 | Williams et al. | |
| 2016/0051847 A1 | 2/2016 | Zhang et al. | |
| 2016/0317044 A1 | 11/2016 | Wu | |
| 2017/0107500 A1 | 4/2017 | Tsakraklides et al. | |
| 2017/0136205 A1 | 5/2017 | Rusher | |
| 2018/0243608 A1 | 8/2018 | Jones et al. | |
| 2018/0318642 A1 | 11/2018 | Lunz et al. | |
| 2018/0339122 A1 | 11/2018 | Lunz et al. | |
| 2018/0341706 A1* | 11/2018 | Agrawal | G06V 20/48 |
| 2019/0336085 A1* | 11/2019 | Kayser | A61B 5/447 |
| 2020/0086074 A1 | 3/2020 | Rusher | |
| 2020/0155898 A1 | 5/2020 | Kuronen et al. | |
| 2020/0245873 A1* | 8/2020 | Frank | A61B 5/0823 |
| 2020/0279339 A1* | 9/2020 | Akutagawa | A61B 10/0064 |
| 2020/0388287 A1* | 12/2020 | Anushiravani | A61B 5/4815 |
| 2021/0001135 A1 | 1/2021 | Kaib et al. | |
| 2021/0068668 A1 | 3/2021 | Slyusarenko et al. | |
| 2021/0076966 A1* | 3/2021 | Grantcharov | G06F 16/7867 |
| 2021/0169417 A1 | 6/2021 | Burton | |
| 2021/0290184 A1* | 9/2021 | Ahmed | A61B 5/746 |
| 2022/0057092 A1 | 2/2022 | Mou et al. | |
| 2022/0192513 A1* | 6/2022 | Atlas | A61B 5/0002 |
| 2022/0331659 A1 | 10/2022 | Chen et al. | |
| 2022/0401672 A1 | 12/2022 | Trumbower et al. | |
| 2023/0041220 A1 | 2/2023 | Iyer et al. | |

OTHER PUBLICATIONS

Notice of Allowance dated Mar. 27, 2023, corresponding to copending related U.S. Appl. No. 18/076,581, 11 pages.

International Search Report and Written Opinion issued on Jun. 7, 2023, in corresponding International Application No. PCT/US2023/061807, 10 pages.

Office Action issued on Feb. 27, 2024, in related U.S. Appl. No. 18/076,610, 32 pages.

\* cited by examiner

CONTROLLING METHOD FOR MONITORING PHYSIOLOGICAL CONDITION OF FIRST USER AND RELATED PRODUCTS

TECHNICAL FIELD

The present disclosure relates to the technical field of medical treatment, and in particular, to a controlling method for monitoring a physiological condition of a first user, and related products.

BACKGROUND

A respiratory device can be employed for a patient who is unable to ensure enough ventilation by her/his own respiratory efforts, for example, a patient who suffers from a respiratory disease caused by the COVID-19 virus.

Doctors or caregivers may have to visit the patients regularly to learn the physiological conditions of the patients, so as to take proper actions against the deterioration of the physiological conditions.

This background information is provided to reveal information believed by the applicant to be of possible relevance to the present disclosure. No admission is necessarily intended, nor should be construed, that any of the preceding information constitutes prior art against the present disclosure.

SUMMARY

This disclosure provides a controlling method for monitoring a physiological condition of a first user, and related products, which control one or more devices used in monitoring the physiological condition of the first user at the side of the first user, and the physiological condition of the first user can be determined automatically and quickly, so that a second user (e.g., a doctor or a caregiver) does not need to visit the first user frequently to determine the physiological condition of the first user, and thereby the cross-infection between the first user and the second user can be prevented, and the state of the second sensing device can be controlled as required, thereby providing greater flexibility for monitoring the physiological condition of the first user.

In a first aspect, an embodiment of the present disclosure provides a method for monitoring a physiological condition of a first user, where the method is applied in a controller which is communicatively connected to at least one first sensing device and a second sensing device; the second sensing device is capable of operating in a first state and a second state, and switching between the first state and the second state is controlled by the controller; where the method includes:
  obtaining first sensing data of the first user reported by the at least one first sensing device;
  determining the physiological condition of the first user based on a result derived from the first sensing data and a reference range corresponding to the first sensing data, where the reference range is related to a physiological state of the first user; and
  upon determining that the physiological condition of the first user is abnormal, sending a control instruction to the second sensing device to switch the second sensing device from the first state to the second state.

In a second aspect, an embodiment of the present disclosure provides a controlling apparatus, which is communicatively connected to at least one first sensing device and a second sensing device, the second sensing device is capable of operating in a first state and a second state, and switching between the first state and the second state is controlled by the controlling apparatus; and the controlling apparatus includes:
  an obtaining module, configured to obtain first sensing data of a first user reported by the at least one first sensing device;
  a determining module, configured to determine a physiological condition of the first user based on a result derived from the first sensing data and a reference range corresponding to the first sensing data, where the reference range is related to a physiological state of the first user; and
  a sensing module, configured to send a control instruction to the second sensing device to switch the second sensing device from the first state to the second state upon determining, by the determining module, that the physiological condition of the first user is abnormal.

In a third aspect, an embodiment of the present disclosure provides a controller, including a processor and a memory, where the processor and the memory are coupled to at least one first sensing device and a second sensing device; the second sensing device is capable of operating in a first state and a second state, and switching between the first state and the second state is controlled by the controller; and the memory is configured to store therein computer instructions which, when executed by the processor, enable the processor to:
  obtain first sensing data of a first user reported by the at least one first sensing device;
  determine a physiological condition of the first user based on a result derived from the first sensing data and a reference range corresponding to the first sensing data, where the reference range is related to a physiological state of the first user; and
  upon determining that the physiological condition of the first user is abnormal, send a control instruction to the second sensing device to switch the second sensing device from the first state to the second state.

In a fourth aspect, an embodiment of the present disclosure provides a system for monitoring a physiological condition of a first user, including a controller, at least one first sensing device, and a second sensing device; where the controller is communicatively connected to the at least one first sensing device and the second sensing device; the second sensing device is capable of operating in a first state and a second state, and switching between the first state and the second state is controlled by the controller;
  where the controller is configured to:
  obtain first sensing data of the first user reported by the at least one first sensing device; and
  determine the physiological condition of the first user based on a result derived from the first sensing data and a reference range corresponding to the first sensing data, where the reference range is related to a physiological state of the first user;
  upon determining that the physiological condition of the first user is abnormal, send a control instruction to switch the second sensing device from the first state to the second state;
  where the first sensing device is configured to:
  acquire the first sensing data; and
  report the first sensing data to the controller;
  where the second sensing device is configured to:
  receive the control instruction; and
  switch from the first state to the second state.

In a fifth aspect, an embodiment of the present disclosure provides a non-transitory computer-readable storage medium, storing therein computer-executable instructions which, when being executed by a processor, implement the method for monitoring a physiological condition of a first user according to the first aspect.

It should be understood that the content described in this section is not intended to identify the key or important features of the embodiments of the present disclosure, nor to limit the scope of the present disclosure. Other features of the present disclosure will be easily understood through the following description.

BRIEF DESCRIPTION OF THE DRAWINGS

The drawings are used for a better understanding of the present solution but do not constitute any limitation on the present disclosure. In the drawings.

DETAILED DESCRIPTION OF THE EMBODIMENTS

Figure 1:
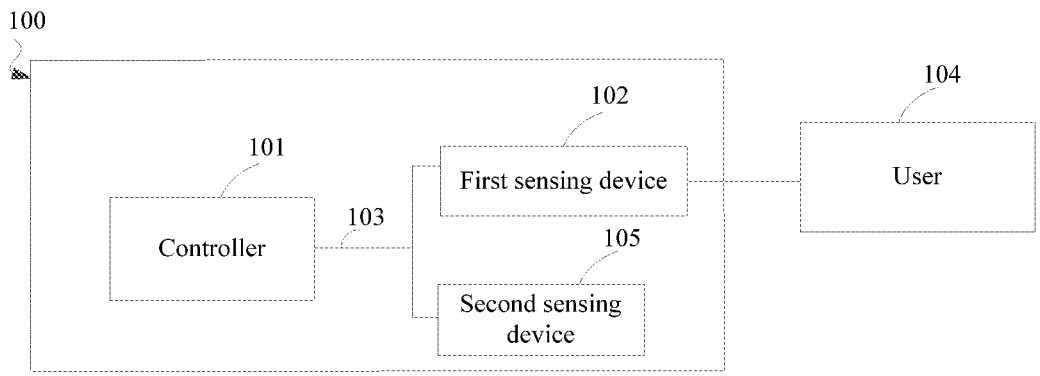
FIG. 1 is an exemplary schematic diagram of a monitoring system according to an embodiment of the present disclosure.

In the following description, reference is made to the accompanying figures, which form part of the disclosure, and which show, by way of illustration, specific aspects of embodiments of the present disclosure or specific aspects in which embodiments of the present disclosure may be used. It is understood that embodiments of the present disclosure may be used in other aspects and include structural or logical changes not depicted in the figures. The following detailed description, therefore, is not to be taken in a limiting sense, and the scope of the present disclosure is defined by the appended claims.

For instance, it is understood that a disclosure in connection with a described method may also hold true for a corresponding device or system configured to perform the method and vice versa. For example, if one or a plurality of specific method steps are described, a corresponding device may include one or a plurality of units, e.g. functional units, to perform the described one or plurality of method steps (e.g. one unit performing the one or plurality of steps, or a plurality of units each performing one or more of the plurality of steps), even if such one or more units are not explicitly described or illustrated in the figures. On the other hand, for example, if a specific apparatus is described based on one or a plurality of units, e.g. functional units, a corresponding method may include one step to perform the functionality of the one or plurality of units (e.g. one step performing the functionality of the one or plurality of units, or a plurality of steps each performing the functionality of one or more of the plurality of units), even if such one or plurality of steps are not explicitly described or illustrated in the figures. Further, it is understood that the features of the various exemplary embodiments and/or aspects described herein may be combined with each other unless specifically noted otherwise.

In the embodiments of the present disclosure, expressions such as "for example" are used to indicate the illustration of an example or an instance. In the embodiments of the present disclosure, any embodiment or design scheme described as "for example" should not be interpreted as preferred or advantageous over other embodiments or design schemes. In particular, the use of "for example" is aimed at presenting related concepts in a specific manner.

In the treatment of respiratory diseases, doctors or caregivers may have to visit the bedside of patients regularly to learn the physiological conditions of the patients, so as to take proper actions against deterioration of the conditions.

However, the frequent visits to the bedside of patients are limited by the human resource capacity in the hospitals, especially in the case that a surge of patients due to the COVID-19 pandemic around the world.

Furthermore, the frequent visits to the patients may cause cross-infection, and may still be insufficient for the doctors or caregivers to capture the occurrence of acute edema signs promptly. Therefore, an automated solution to monitor the physiological condition of patients is desired.

In view of the above problem, the present disclosure provides a method for monitoring a physiological condition of a first user (e.g., a patient). According to the method, the physiological condition of the first user can be determined automatically and quickly, so that a second user (e.g., a doctor, a caregiver, or a relative or friend of the first user) does not need to visit the first user frequently to determine the physiological condition of the first user, and thereby the cross-infection between the first user and the second user can be prevented.

Before elaborating on the embodiments of the present disclosure, an exemplary scenario to which the embodiments are applicable will be described in the first place.

FIG. 1 is an exemplary schematic diagram of a monitoring system according to an embodiment of the present disclosure. With reference to FIG. 1, a monitoring system 100 includes a controller 101, at least one first sensing device 102, and a second sensing device 105. The controller 101 is communicatively connected to the at least one first sensing device 102 and the second sensing device 105. At least one first sensing device 102 may transmit first sensing data to the controller 101 via a communication connection 103, such as a direct wired or wireless connection, or via any kind of network, e.g. a wired or wireless network or any combination thereof, or any kind of private and public network, or any kind of combination thereof, where the first sensing data may reflect a physiological condition or state of a user 104 who uses the monitoring system 100 (Here the user refers to the one who is being monitored). The controller 101 may control the operations of at least one first sensing device 102, receive the first sensing data from the at least one first sensing device 102, and determine the physiological condition of the user based on the first sensing data. The second sensing device 105 may transmit second sensing data to the controller 101 via the communication connection 103, the controller 101 may control the operations of the second sensing device 105 and receive the second sensing data from the second sensing device 105.

In an embodiment, the at least one first sensing device 102 may include a pressure sensor configured for measuring the heart beat and/or pulsing movement of the user 104, a sensor measuring the breath rate of the user 104, a motion sensor measuring respiratory muscle movement of the user 104, a motion sensor measuring physical movement of the user 104, an auditory sensor configured for measuring coughing sound of the user 104, an audio sensor measuring the respiratory lung sound of the user 104, a blood oxygen (SpO2) sensor measuring the blood oxygen level of the user 104, etc. In a possible implementation, the at least one first sensing device 102 may be a continuously working sensing device. In a possible implementation, the at least one first sensing device 102 may be an intermittently working sensing device or a periodically working sensing device.

In a possible implementation, the second sensing device 105 is capable of switching between a first state and a second state, the number of the second sensing device 105 is one or more, and the second sensing device 105 may be a video capturing device and/or an audio detection device controlled by the controller 101 to acquire video data and/or verbal communication data of the user.

It is understood that FIG. 1 is merely a logical schematic diagram of the monitoring system 100, which shows an exemplary configuration of functional units. In a practical application scenario, the function units of the system may be implemented in various forms, which are not limited by the embodiments of the present disclosure.

Figure 2:
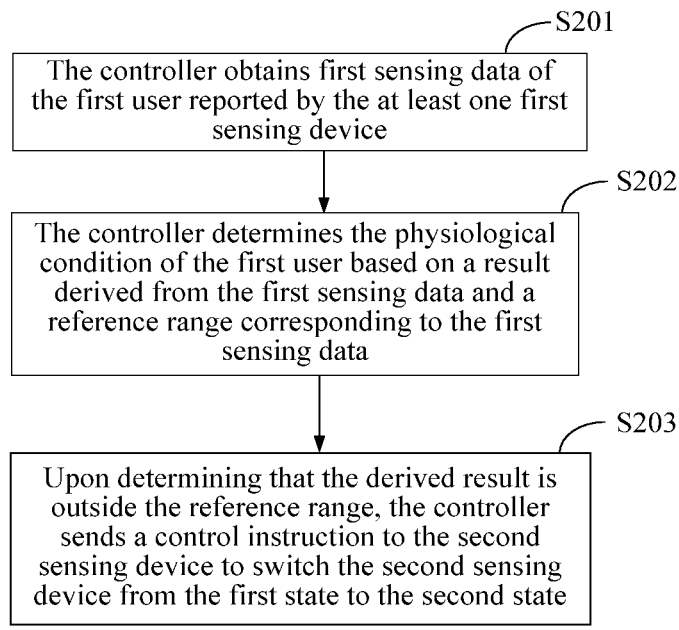
FIG. 2 is a schematic flowchart of a method for monitoring a physiological condition of a first user according to an embodiment of the present disclosure.

FIG. 2 is a schematic flowchart of a method for monitoring a physiological condition of a first user according to an embodiment of the present disclosure. The first user is a person who uses the monitoring system 100, for example, a patient who suffers from respiratory disease, including a patient caused by the COVID-19 virus in critical or severe condition or with the mild symptom and so on, which will not be limited in the embodiments of the present disclosure.

The method may be applied in the monitoring system 100 shown in FIG. 1, and more specifically, applied in the controller 101 that is communicatively connected to the at least one first sensing device 102 and the second sensing device 105. The second sensing device 105 is capable of operating in a first state and a second state, and switching between the first state and the second state of the second sensing device 105 is controllable by the controller. The method for monitoring the physiological condition of the first user includes the steps as follows.

Step S201, the controller obtains first sensing data of the first user reported by the at least one first sensing device.

The controller in the present disclosure is generally configured to gather measurement data (e.g., the first sensing data of the first user) from the user side, so as to perform analysis based on the gathered data.

Step S202, the controller determines the physiological condition of the first user based on a result derived from the first sensing data and a reference range corresponding to the first sensing data, where the reference range is related to a physiological state of the first user.

Upon acquiring the first sensing data, the controller may perform preprocessing on the first sensing data to derive the result of the preprocessing from the first sensing data, and then the controller may perform an analysis of the result derived from the first sensing data to determine the physiological condition of the first user. Here, as described above, the analysis may be performed not only on the result derived from the first sensing data, but also on a reference range as well. The factors such as an age, gender, a medical condition, and a historical physiological condition of the first user, a physiological parameter measured by the first sensing device, movements of the user and so on would be reflected in the reference range and further influence the determination of the physiological condition of the first user.

Specifically, the reference range is related to the physiological state of the first user. For example, the reference range may refer to a normal range of a physiological parameter measured by the first sensing device of the first user who is in a normal physiological condition, that is, the reference range is the normal range of the first sensing data. The normal physiological condition of the first user may refer to a condition that there is no occurrence of sudden (acute) signs and symptoms, such as difficulty breathing (dyspnea) or extreme shortness of breath that worsens with activity or when lying down; a feeling of suffocating or drowning that worsens when lying down; a cough that produces frothy sputum that may be tinged with blood; wheezing or gasping for breath; anxiety, restlessness or a sense of apprehension; bluish lips; a rapid, irregular heartbeat, etc. The reference range may be preset and stored in the controller, e.g., in a storage unit of the controller, in a memory independent of the controller, or stored in a cloud server, which is not limited in the embodiments of the present disclosure. In the case where the reference range is stored in the cloud server, the controller may interact with the cloud server to get the reference range.

Step S203, upon determining that the physiological condition of the first user is abnormal, the controller sends a control instruction to the second sensing device to switch the second sensing device from the first state to the second state.

Based on the result derived from the first sensing data and the reference range corresponding to the first sensing data, the physiological condition of the user can be determined, and the controller sends the control instruction to the second sensing device to switch the second sensing device from the first state to the second state.

In a possible implementation, the first state of the second sensing device is a sleeping state, and the second state of the second sensing device is a working state. In another possible implementation, the first state and the second state of the second sensing device are both working states, but with different working mechanisms.

In a possible implementation, the second sensing device may be a video capturing device and/or an audio detection device. For example, the second sensing device may be a camera used for capturing video data of the first user to enable a doctor or a caregiver (which may be referred to as a second user in the present disclosure) to observe visually on the first user when needed via a communication link between the monitoring device at the first user side and a remote device at the side of the doctor or caregiver, where the communication link may be any kind of network, e.g. a wired or wireless network or any combination thereof, or any kind of private and public network, or any kind of combination thereof For another example, the second sensing device may be an auditory sensor, which may also include a speaker that may receive voice data of the first user, and enable the first user to conduct a verbal communication with the doctor or the caregiver when needed via the communication link between the monitoring device at the first user side and a remote device at the side of the doctor or the caregiver. In a possible implementation, the auditory sensor may be disposed on the breathing circuit, such as a face mask, a nasal cannula, a tube for respiratory gas delivery, etc.

According to the method for monitoring the physiological condition of the first user explained in the embodiment of the present disclosure, the controller obtains the first sensing data of the first user reported by the at least one first sensing device, and determines the physiological condition of the first user based on the result derived from the first sensing data and the reference range corresponding to the first sensing data, then upon determining that the physiological condition of the first user is abnormal, the controller sends the control instruction to the second sensing device to switch the second sensing device from the first state to the second state, through which, on the one hand, the physiological condition of the first user can be determined automatically and quickly, so that the second user does not need to visit the first user frequently to determine the physiological condition of the first user, and thereby the cross-infection between the first user and the second user can be prevented; on the other hand, the state of the second sensing device can be controlled as required, thereby providing greater flexibility for monitoring the physiological condition of the first user.

Figure 3:
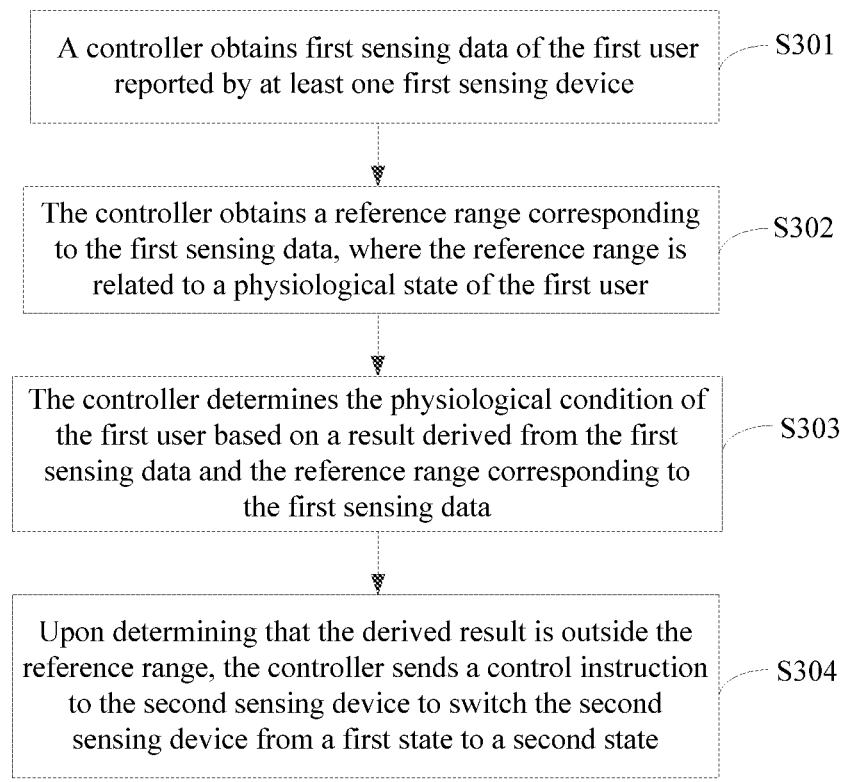
FIG. 3 is a schematic flowchart of another method for monitoring a physiological condition of a first user according to an embodiment of the present disclosure.

FIG. 3 is a schematic flowchart of another method for monitoring a physiological condition of a first user according to an embodiment of the present disclosure. Specifically, the method may include the following steps.

The method includes the steps described in the following. Some of the steps which have already been explained in the embodiment corresponding to FIG. 2 will not be elaborated again for conciseness. The method may be applied in the monitoring system shown in FIG. 1.

Step S301, a controller obtains first sensing data of the first user reported by at least one first sensing device.

In a possible implementation, the first sensing data may include physiological information obtained from the at least one first sensing device. In a possible implementation, the first sensing device includes at least one of the following: a SpO2 sensor, a breath rate sensor, a heart rate sensor, a respiratory muscle motion detection sensor, a cough detection sensor, a body movement sensor, and a lung sound detection sensor.

In a possible implementation, the first sensing data includes at least one of the following: a respiratory rate, a heart rate, blood oxygen saturation, and sound data. Where the respiratory rate is an important parameter in the field of respiration monitoring and may indicate the number of breaths the first user takes within a period of time, such as breaths per minute.

In a possible implementation, the sound data may include at least one of a duration, a frequency, and a sound amplitude of a coughing sound, a wheezing sound, a crackling sound, a rhonchi sound amplitude, and a whooping sound. These sound data may provide vital information on the severity of symptoms of the first user, for example, cough-related information (including the duration, the frequency, and the amplitude of the coughing sound mentioned above) may indicate when intervention is needed from a doctor or caregiver, and compared with the detection of blood oxygen saturation, the detection of cough-related information is more effective in providing feedback on the severity of the first user suffered from respiratory disease.

Step S302, the controller obtains a reference range corresponding to the first sensing data, where the reference range is related to a physiological state of the first user.

In a possible implementation, the controller may obtain the reference range according to input from the second user. Specifically, the reference range may be preset by the second user through an external inputting apparatus. For example, a doctor may preset the reference range based on his/her experiences by using an external inputting device via a network. In a possible implementation, the reference range is pre-set by the second user according to at least one of an age, gender, medical condition, and historical physiological condition of the first user, and a physiological parameter measured by the first sensing device.

In a possible implementation, the at least one first sensing device includes a SpO2 sensor, the reference range for the first sensing data from the SpO2 sensor is between a first upper limit and a second lower limit pre-set by a second user (e.g., a doctor or a caregiver), where the first upper limit is within a range of 95-99%, and the second lower limit is within a range of 84-93%.

In a possible implementation, the at least one first sensing device includes a breath rate sensor, the reference range for the first sensing data from the breath rate sensor is between a third upper limit and a fourth lower limit; the third upper limit is selected by the second user between 20-25 beats per minute, and the fourth lower limit is selected by the second user between 9-15 beats per minute.

In a possible implementation, the external inputting apparatus for receiving the input from the second user may be integrated into a device for monitoring the physiological condition of the first user which is configured to perform the method for monitoring the physiological condition of the first user, and the external inputting apparatus may be a keyboard and pointing apparatus (for example, a mouse or a trackball) through which the second user can provide input to the computer, which is not limited in the embodiments of the present disclosure.

In a possible implementation, the reference range is obtained as follows:

in response to detecting that the first user is substantially in a peace state, the controller determines the reference range according to a first setting;

in response to detecting that the first user is substantially in a moving state, the controller determines the reference range according to a second setting.

In a possible implementation, the determining of the reference range by the controller may be done every preset monitoring interval, that is, the above detection may be done at each monitoring interval.

Before determining the reference range based on different settings, baseline data corresponding to the first user may be obtained based on an age of the first user in the first place.

The baseline data generally refers to data of users under normal physiological conditions, for example, when they are not suffering from diseases, and this baseline data serves as a basis for determining the reference range of a specific user.

In the following, a detailed description will be made with respect to how to obtain the baseline data by taking an example where the baseline data relates to a respiratory rate. That is to say, in this example, the baseline data is related to the respiratory rate, but the baseline data may be related to other physiological parameters measured by at least one first sensing device, which is not limited to the embodiments of the present disclosure. That is to say, the following description is also applicable to other kinds of data, with little modification if necessary.

Ranges of normal respiratory rates of healthy people within different age groups are shown in Table 1 below. The healthy people in the present disclosure may refer to people without suffering diseases (such as respiratory diseases) affecting the normal respiratory rate.

TABLE 1

| Age group | Age-related respiratory rate range |
| --- | --- |
| Newborn to 12 Months | 30 to 60 breaths per minute |
| 1 to 2 Years old | 24 to 40 breaths per minute |
| 3 to 5 Years old | 22 to 34 breaths per minute |
| 6 to 12 Years old | 18 to 30 breaths per minute |
| 13 to 17 Years old | 12 to 20 breaths per minute |
| 18 years old and higher | 12 to 20 breaths per minute |

As shown in Table 1, healthy people within different age groups may have different ranges of normal respiratory rates. Based on this, in a possible implementation, the controller may obtain the baseline data corresponding to the first user based on the age of the first user, so as to further obtain the reference range of the first user on the basis of the baseline data. For example, if the age of the first user is 15 years old, that is, within the age groups of 13 to 17 years old, the baseline data corresponding to the first user may be 12 to 20 breaths per minute.

In a possible implementation, the baseline data may also correspond to a respiratory rate range covering all age groups, for example, the baseline data may be 12 to 60 breaths per minute according to Table 1.

The baseline data would be acquired in several possible ways. In a possible implementation, the controller can obtain the baseline data from a local database integrated into the controller, the database may pre-store a corresponding relationship between an age group and an age-related respiratory rate range, for example, the corresponding relationship as shown in Table 1. In a possible implementation, the controller can obtain the baseline data from a cloud. The baseline data stored in the cloud may be generated by a cloud server. The cloud server may generate the baseline data by comprehensively analyzing multi-user data using an artificial intelligence (AI) algorithm. In response to the request for obtaining the baseline data from the controller, the cloud can send the latest baseline data to the controller.

In a possible implementation, after obtaining the baseline data, the controller can determine the reference range according to the first setting or the second setting.

In a possible implementation, the first setting refers to determine the reference range as follows:
  determining the reference range corresponding to the first sensing data based on a historical condition of the first user and the baseline data in response to detecting that the first user is substantially in the peace state.

In a possible implementation, the second setting refers to determine the reference range as follows:
  determining a first range corresponding to the first user based on a historical condition of the first user and the baseline data, and adjust the first range with a preset margin to obtain the reference range in response to detecting that the first user is substantially in the moving state.

It should be understood by those skilled in the art that the respiratory rate of a man in different physical states may be different, for example, the respiratory rate of a man in a moving state is higher than the respiratory rate of a man in a peace state. The peace state is relative to the moving state, such as rest, sleep, etc. The measurement data of users in different physical states will be taken into account in this implementation of the present disclosure.

In a possible implementation, the measurement data includes movement information indicating the physical state of the first user and can be obtained from, e.g., a motion sensor, that is, the at least one first sensing device may include a motion sensor. For example, the motion sensor may be an accelerometer, a gyro-sensor, a magnetic sensor, etc., which may be configured for measuring movement information that indicates the physical state of the first user. The controller can detect the physical state of the first user based on the movement information, and determine the reference range corresponding to the first sensing data in response to detecting different physical states of the first user.

First Setting

The controller can determine the reference range corresponding to the first sensing data based on the historical condition of the first user and the baseline data, in response to detecting that the first user is substantially in the peace state (e.g., during a respective monitoring interval), where the term "substantially" may mean that for a monitoring interval, the first user is in the peace state most of the time, not absolutely all the time.

In a possible implementation, if the first user is a healthy person (which means that the historical condition of this user reflects that this user is healthy), and the controller detects that the first user is substantially in the peace state (e.g., during a respective monitoring interval), the controller can take the determined baseline data mentioned above as the reference range directly.

In a possible implementation, if the first user is an unhealthy person (which means that the historical condition of this user reflects that this user is unhealthy), and the controller detects the first user is substantially in the peace state, the controller can determine the reference range corresponding to the first sensing data by synthesizing the historical condition of the first user and the baseline data. For example, based on the historical condition of the first user, the first user is determined to be a user with respiratory disease (or other diseases), and the respiratory rate of the first user in the peace state without the occurrence of sudden (acute) signs and symptoms may be higher than the normal respiratory rate of healthy people, e.g., 20% higher, in this case, the reference range corresponding to the first sensing data can be determined to be 20% higher than the baseline data, that is, the reference range may be obtained through increasing the baseline data with a first margin of 20%. In a possible implementation, the first margin can be pre-set by the second user.

Second Setting

The controller can determine the first range corresponding to the first user based on a historical condition of the first user and the baseline data, and adjust the first range with a preset margin (second margin) to obtain the reference range, in response to detecting that the first user is substantially in a moving state (e.g., during a respective monitoring interval). In a possible implementation, the second margin can be preset by the second user. Specifically, the first range corresponding to the first user refers that the first range is related to a historical condition of the first user.

In a possible implementation, if the first user is a healthy person (which means that the historical condition of this user reflects that this user is healthy), and the controller detects the first user is substantially in the moving state, the controller can take the determined baseline data (which may be referred to as the normal respiratory rate of healthy people in the peace state) mentioned above as the first range corresponding to the first user, and adjust the first range with the second margin to obtain the reference range.

For example, based on the historical condition of the first user, the first user is determined to be a user without a respiratory disease (or other diseases), and the respiratory rate of the first user in the moving state may be substantially equal to the respiratory rate of the first user in the moving state corresponding to the historical condition of the first user, in this case, the baseline data (which may be referred to as the normal respiratory rate of healthy people in the peace state) may be determined as the first range, and the reference range corresponding to the first sensing data can be obtained through adjusting the first range with the second margin. For an instance, based on the historical condition of the first user, the respiratory rate of the first user without respiratory disease (or other diseases) in the moving state may be higher than the normal respiratory rate of healthy people, e.g., 5% higher, in this case, the reference range corresponding to the first sensing data can be determined to be 5% higher than the baseline data, this is, the reference range may be obtained through increasing the baseline data (i.e., the first range) with a margin of 5%.

In a possible implementation, if the first user is an unhealthy person (which means that the historical condition of this user reflects that this user is unhealthy), and the controller detects the first user is substantially in the moving state, the controller can determine the first range corresponding to the first user through synthesizing a historical condition of the first user and the baseline data (which may refer to as the normal respiratory rate of healthy people in the peace state) and adjust the first range with the second margin to obtain the reference range. For example, based on the historical condition of the first user, the first user is determined to be a user with respiratory disease (or other diseases), and the respiratory rate of the first user in the moving state without the occurrence of sudden (acute) signs and symptoms may be substantially equal to the respiratory rate of the first user in the moving state corresponding to the historical condition of the first user, which may be higher than the normal respiratory rate of healthy people in the moving state, e.g., 4% higher due to respirator disease (or other disease), in this case, the normal respiratory rate of healthy people in the moving state may be determined as the first range, which may be obtained through increasing the baseline data that corresponds to the normal respiratory rate of healthy people in the peace state, and the reference range corresponding to the first sensing data can be obtained through adjusting the first range with the second margin, for example, the reference range corresponding to the first sensing data can be determined to be 4% higher than the first range, that is, the reference range may be obtained through increasing the first range with a margin of 4%.

As described above, the second margin corresponding to a healthy person or an unhealthy person may be different. Therefore, the second margin may have different values.

The historical condition of the first user may be the past healthy condition of the first user, which may include historical cases of the first user, and measurement data records of physiological parameters (e.g., respiratory rate) of the first user in the peace state and the moving state (with and without the occurrence of sudden (acute) signs and symptoms), etc. The historical condition of the first user and the first and second margin may be stored in a local database or cloud in a similar way as the storage mode of the baseline data, which will not be described in detail for the sake of brevity.

Step S303, the controller determines the physiological condition of the first user based on a result derived from the first sensing data and the reference range corresponding to the first sensing data, where the reference range is related to a physiological state of the first user.

Figure 4:
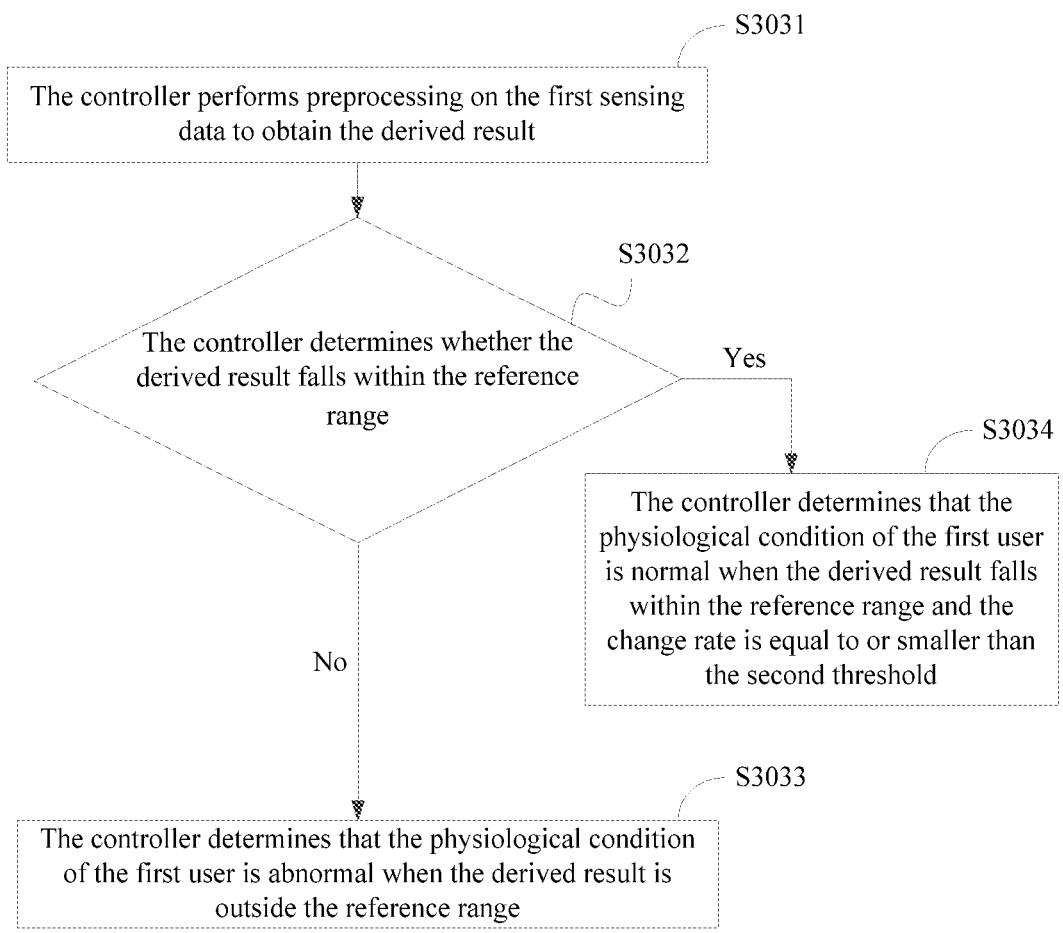
FIG. 4 is a schematic flowchart of a process for determining a physiological condition of a first user according to an embodiment of the present disclosure.

In a possible implementation, step S303 may include steps as shown in FIG. 4, which is a schematic flowchart of a process for determining a physiological condition of a first user according to an embodiment of the present disclosure.

Step S3031, the controller performs preprocessing on the first sensing data to obtain the result derived from the first sensing data.

In order to screen out real first sensing data that could be used for the determination of the physiological condition of the first user, the controller performs preprocessing on the first sensing data, to obtain the result derived from the first sensing data.

In a possible implementation, the preprocessing may include at least one of the following: data set selection, data compression, data filtering, data cleaning, etc. The data set selection may refer to selecting a data set corresponding to a certain time period, such as a data set corresponding to 8:00-8:30 am. The data compression refers to a technology to reduce the amount of data to reduce storage space or reorganize the data according to a certain algorithm to reduce data redundancy and storage space without losing useful information. The data cleaning refers to discarding a piece of data without analyzing thereon, for example, the EKG-artifact (Electrocardiogramtifact, EKG-artifact for short) in Electrocardiogramata may be discarded directly without analyzing thereon. Different from data cleaning, data filtering may refer to filtering out abnormal data based on analysis. Of course, other processing may also be used herein for preprocessing, as long as the invalid measurement data is removed as required.

Step S3032, the controller determines whether the result derived from the first sensing data falls within the reference range.

As a possible implementation, the at least one first sensing device includes multiple first sensing devices configured to measure physiological data of the first user, specifically, the number of the first sensing devices is more than one.

Before the controller determines whether the result derived from the first sensing data falls within the reference range based on the first sensing data from the multiple first sensing devices, the controller can calculate an average value of the filtered first sensing data reported by the multiple first sensing devices to obtain the result derived from the first sensing data. The step of calculating the average value mentioned above is performed for the filtered first sensing data reported by each of the multiple first sensing devices, and if the filtered first sensing data includes multiple types of data, such as a respiratory rate, a heart rate, a blood oxygen saturation, sound data and so on, the step of calculating the average value is performed for each type of data, that is, there would be an average value corresponding to each type of data.

In a possible implementation, still, on the premise that the at least one first sensing device includes multiple first sensing devices configured to measure physiological data, the controller determines whether the result derived from the first sensing data falls within the reference range, including the following operations:

for each of the multiple first sensing devices, the controller determines whether a temporary result derived from the first sensing data falls within the reference range;

the controller counts a first number of first sensing device, among the multiple first sensing devices, whose temporary result derived from the first sensing data falls within the reference range;

the controller counts a second number of first sensing device, among the multiple first sensing devices, whose temporary result derived from the first sensing data is outside the reference range; and if the first number is equal to or greater than the second number, the controller determines that the result derived from the first sensing data falls within the reference range.

Here counting the first number and the second number serves to improve the accuracy of determining whether the result derived from the first sensing data falls within the reference range.

An example is taken, assuming that the at least one first sensing device includes three first sensing devices configured to measure physiological data (e.g., a respiratory rate, a heart rate, or the like), if the temporary results derived from the first sensing data corresponding to two of the three first sensing devices both fall within the reference range, but the temporary result derived from the first sensing data corresponding to one first sensing device is outside the reference range, that is, the first number mentioned above is two, which is greater than the second number mentioned above (which is one), then the controller determines that the result derived from the first sensing data mentioned in step S303 falls within the reference range, that is, the conclusive result derived from first sensing data corresponding to the three first sensing devices is considered to fall within the reference range; or if the temporary result derived from the first sensing data corresponding to one of the three first sensing devices falls within the reference range, but the temporary results derived from the first sensing data corresponding to two first sensing devices are both outside the reference range, that is, the first number is one, which is not equal to or greater than the second number (which is two), then the controller determines that the result derived from the first sensing data mentioned in step S303 is outside the reference range, that is, the conclusive result derived from first sensing data corresponding to the three first sensing devices is considered to be outside the reference range.

Another example is taken, assuming that the at least one first sensing device includes two first sensing devices configured to measure physiological data (e.g., a respiratory rate, a heart rate or the like), if the result derived from the first sensing data corresponding to one first sensing device falls within the reference range, but the result derived from the first sensing data corresponding to another first sensing device is outside the reference range, that is, the first number is one, which is equal to the second number (which is also equal to one), then the controller determines that the result derived from the first sensing data mentioned in step S303 falls within the reference range, that is, the conclusive result derived from first sensing data corresponding to the two first sensing devices is considered to fall within the reference range.

In this implementation, the number of the first sensing devices configured to measure physiological data may be other values, which are not limited by the embodiments of the present disclosure.

Step S3033, the controller determines that the physiological condition of the first user is abnormal when the result derived from the first sensing data is outside the reference range.

In a possible implementation, when it is determined by the controller that the result derived from the first sensing data is outside the reference range in step S3032, the controller determines that the physiological condition of the first user is abnormal. In a possible implementation, if the first sensing device includes multiple first sensing devices (i.e., the number of the first sensing devices is more than one), and the result derived from the first sensing data (that is, the conclusive result derived from the first sensing data corresponding to the multiple first sensing devices) is considered to be outside the reference range, the controller determines that the physiological condition of the first user is abnormal.

As a possible implementation, under the scenario where the at least one first sensing device includes multiple first sensing devices configured to measure physiological data, the abnormal condition of the first user can be determined through a change rate of the physiological data as follows.

Specifically, step S302 of determining the physiological condition of the first user based on the result derived from the first sensing data and the reference range corresponding to the first sensing data may include: the controller calculates a change rate of the result derived from the first sensing data, determines whether the change rate is greater than a second threshold; and when the result derived from the first sensing data falls within the reference range and the change rate is greater than the second threshold, determines that the physiological condition of the first user is abnormal. In a possible implementation, the at least one first sensing device is configured for measuring a respiratory parameter (i.e., first sensing data) of the first user, and the pre-processing is performed on the respiratory parameter to obtain the processed respiratory (i.e., the result derived from the first sensing data). For example, the at least one first sensing device is configured for measuring a respiratory rate, the controller performs preprocessing on the respiratory rate to obtain the processed respiratory rate, and the condition of the first user is determined to be abnormal when the change rate of the processed respiratory rate is relatively large, even if the processed respiratory rate (i.e., the result derived from the respiratory rate) falls within the reference range.

Step S3034, the controller determines that the physiological condition of the first user is normal when the result derived from the first sensing data falls within the reference range and the change rate is equal to or smaller than the second threshold.

In another possible implementation, when it is determined by the controller that the result derived from the first sensing data falls within the reference range in step S3032, and the change rate is equal to or smaller than the second threshold mentioned above, then the controller determines that the physiological condition of the first user is normal.

With the method mentioned above, whether the result derived from the first sensing data is outside the reference range can be determined. Under the determination that the result derived from the first sensing data is outside the reference range, the method for monitoring the physiological condition of the first user includes step S304 as follows.

Step S304, upon determining that the physiological condition of the first user is abnormal, the controller sends a control instruction to the second sensing device to switch the second sensing device from a first state to a second state.

In a possible implementation, the controller is further communicatively connected to at least one data storage device connected to the second sensing device. In a possible implementation, the at least one data storage device includes at least a long-term memory section and a short-term memory section; the controller is capable of storing second sensing data from the second sensing device selectively to the long-term memory section or the short-term memory section.

In a possible implementation, the second sensing device and the at least one data storage device may be discrete devices. In a possible implementation, the second sensing device and the at least one data storage device may be integrated into one device, for example, the at least one data storage device may be integrated into the second sensing device.

In a possible implementation, the second sensing device and the at least one data storage device are discrete devices, the at least one data storage device can be communicatively connected to the at least one first sensing device and the second sensing device, and the controller is capable of storing the first sensing data from the at least one first sensing device and the second sensing data from the second sensing device selectively to the long-term memory section or the short-term memory section.

In a possible implementation, the first state of the second sensing device is a sleeping state or a short-term state, the second state of the second sensing device is a long-term state, and the control instruction is further used to instruct the second sensing device to store the second sensing data to the long-term memory section of the at least one data storage device. Specifically, the short-term state of the second sensing device refers to a working state that the second sensing device stores the second sensing data to the short-term memory section of the data storage device, and the long-term state of the second sensing device refers to another working state that the second sensing device stores the second sensing data to the long-term memory section of the data storage device. The short-term memory section refers to a memory section that stores a small amount of information in a short period of time (e.g., one minute). The long-term memory section is a concept relative to the short-term memory section and refers to a memory section that stores information over a long period of time (e.g., a period of time more than one minute). The period of time that the short-term memory section or the long-term memory section can store data can be preset by the second user, which will not be limited by the embodiments of the present disclosure.

When the controller determines that the physiological condition of the first user is normal, the second sensing device can be in the sleeping state to save power, and upon determining that the physiological condition of the first user is abnormal, the controller can send the control instruction to the second sensing device to switch the second sensing device from the sleeping state (i.e., the first state) to the long-term state (i.e., the second state), so that the second sensing device starts to work and store the second sensing data to the long-term memory section of the data storage device. Alternatively, when the controller determines that the physiological condition of the first user is normal, the second sensing device can be in the short-term state and store the second sensing data to the short-term memory section of the data storage device, so that the storage space of the data storage device can be saved, and upon determining that the physiological condition of the first user is abnormal, the controller can send the control instruction to the second sensing device to switch the second sensing device from the short-term state (i.e., the first state) to the long-term state (i.e., the second state), so that the second sensing device starts to store the second sensing data to the long-term memory section of the data storage device.

In a possible implementation, when the first state of the second sensing device is the short-term state, the control instruction is further used to copy the second sensing data of the second sensing device from the short-term memory section to the long-term memory section, so that the second user can learn the physical condition of the first user in a period of time before the physiological condition of the first user becomes abnormal. In a possible implementation, the short-term memory section is working in a First-In-First-Out (FIFO for short) mode.

In a possible implementation, upon determining that the physiological condition of the first user returns to normal, the controller can send an instruction to the second sensing device to switch the second sensing device from the second state back to the first state.

Figure 5:
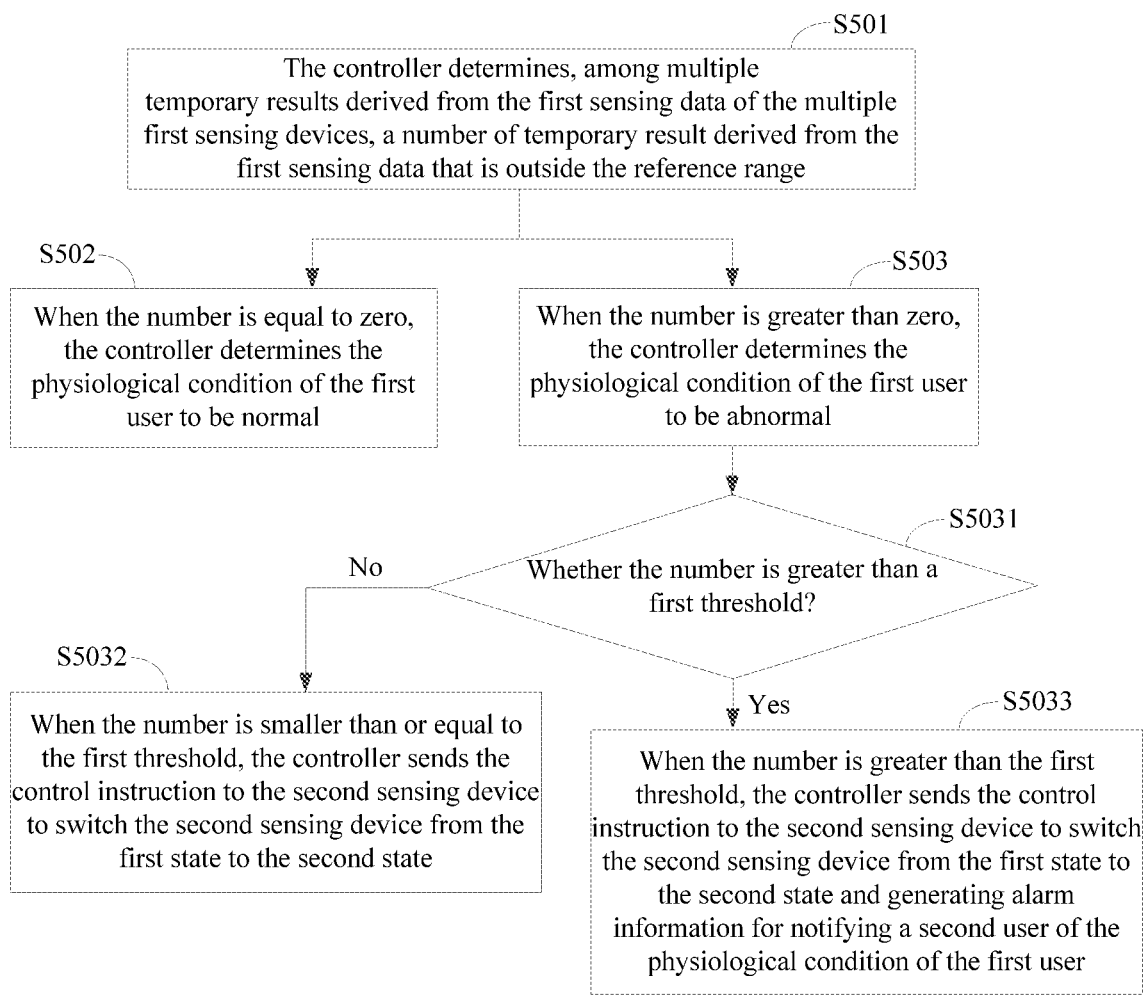
FIG. 5 is a schematic flowchart of another process for determining a physiological condition of a first user according to an embodiment of the present disclosure.

In a possible implementation, at least one first sensing device includes multiple first sensing devices configured for measuring physiological data of the first user, and the method for monitoring the physiological condition of the first user may include steps as shown in FIG. 5:

step S501, the controller determines, among multiple temporary results derived from the first sensing data of the multiple first sensing devices, a number of temporary result derived from the first sensing data that is outside the reference range;

step S502, when the number is equal to zero, the controller determines the physiological condition of the first user to be normal;

step S503, when the number is greater than zero, the controller determines the physiological condition of the first user to be abnormal.

step S5031, upon determining that the physiological condition of the first user is abnormal, the controller determines whether the number is greater than a first threshold;

step S5032, when the number is smaller than or equal to the first threshold, the controller sends the control instruction to the second sensing device to switch the second sensing device from the first state to the second state;

step S5033, when the number is greater than the first threshold, the controller sends the control instruction to the second sensing device to switch the second sensing device from the first state to the second state and generates alarm information for notifying a second user of the physiological condition of the first user.

In the scenario where the at least one first sensing device includes multiple first sensing devices configured to measure physiological data of the first user, in a possible implementation, before step S303 of determining the physiological condition of the first user based on the result derived from the first sensing data and the reference range corresponding to the first sensing data, the controller can average the first sensing data reported by the multiple first sensing devices in a preset number of monitoring intervals. In a possible implementation, the step S303 may include: the controller determines the physiological condition of the first user based on temporary results derived from the averaged first sensing data and the reference range corresponding to the first sensing data. For example, the controller may calculate an average of the last four detected respiratory rates of the first user and determine an average physiological condition of the first user based on the averaged four detected respiratory rates of the first user and the reference range corresponding to the first sensing data. In this case, the controller can determine the physiological condition of the first user by comprehensively analyzing the average physiological condition of the first user in the preset number of monitoring intervals.

In a possible implementation, the controller determines, among the multiple temporary results derived from the first sensing data (i.e., the temporary results derived from the first sensing data corresponding to the multiple first sensing devices), the number of temporary result derived from the first sensing data that is outside the reference range (i.e., the physiological condition of the first user is abnormal).

The determining the physiological condition of the first user based on the result derived from the first sensing data and the reference range corresponding to the first sensing in step S303 may include following steps: firstly, a determination is made whether the number is equal to zero, and when the number is equal to zero, the controller determines the physiological condition of the first user to be normal; secondly, when the number is not equal to zero (i.e., the number is greater than zero), the controller determines the physiological condition of the first user to be abnormal.

Further, the controller can handles the determined result that the physiological condition of the first user is abnormal, for example, in step S303, upon determining that the physiological condition of the first user is abnormal, the controller can send the control instruction to the second sensing device to switch the second sensing device from the first state to the second state. Specifically, in this implementation, step S303 can be further divided to the following operations: firstly, a determination is made whether the number of temporary result derived from the first sensing data that is outside the reference range is greater than a first threshold, and when the number is smaller than or equal to the first threshold (which indicates that the situation is a bit serious), the controller can send the control instruction to the second sensing device to switch the second sensing device from the first state to the second state; when the number is greater than the first threshold (which indicates that the situation is very serious), then the controller can send the control instruction to the second sensing device to switch the second sensing device from the first state to the second state and generate alarm information for notifying a second user of the physiological condition of the first user. Here the first threshold may be pre-set by the second user according to actual needs, and the setting of the first threshold helps to classify the response to abnormal physiological conditions into different levels.

In a possible implementation, the second sensing device includes at least one of a video capturing sensor and an audio detection sensor. In a possible implementation, the video capturing sensor may be any device that can acquire video data of the first user, such as a camera and may be disposed in a position that is able to capture images of the face or the whole body of the first user, which is not limited by the embodiments of the present disclosure. In a possible implementation, the audio detection sensor may be a microphone that can acquire verbal communication data of the first user, and may be disposed in a position that is able to acquire verbal communication data of the first user, for example, a position near the mouth of the first user, which is not limited by the embodiments of the present disclosure. The control instruction is used for triggering the at least one of the video capturing sensor and the audio detection sensor to switch from the sleeping state or the short-term state to the long-term state. The audio detection sensor can be used for oral communication between the first user and the second user, and the audio detection sensor also can be used to acquire the sound data including at least one of a duration, a frequency, and a sound amplitude of a coughing sound, a wheezing sound, a crackling sound, a rhonchi sound amplitude, and a whooping sound as mentioned above.

In a possible implementation, in order to ensure the privacy of the first user, the control instruction can be verified to determine whether the control instruction is authorized, and the second sensing device is switched from the first state to the second state only if the control instruction is authorized. In a possible implementation, the controller may send the control instruction together with a key, which is used to uniquely match the same key pre-stored in the second sensing device. If the matching is successful, the control instruction is authorized. The key may be biometric information of the second user (e.g., a doctor or a caregiver), for example, iris information or fingerprint information. In an optional or alternative implementation, the key may be a numeric, character, or alphabetic password, or a combined password of number, character, or alphabet.

In a possible implementation, the controller may send a second control instruction to the second sensing device after a preset time from sending the control instruction, and the second control instruction is used for triggering the second sensing device to switch from the second state to the first state. Through the second control instruction, the controller may control the second sensing device to automatically switch from the second state to the first state in the case that the second user forgets to conduct the state switching of the second sensing device. In an optional or alternative implementation, the controller may control the state switching between the first state and the second state of the second sensing device upon receiving input from the second user. For example, when the second user thinks that it is not necessary to visually observe and/or orally communicate with the first user to learn information related to the physical state of the first user, the second user can input an instruction to trigger the controller to send the second control instruction to the second sensing device, so that the second sensing device is switched from the second state to the first state.

In a possible implementation, the second sensing device includes a video capturing sensor, and after generating the alarm information for notifying the second user of the physiological condition of the first user, the method for monitoring the physiological condition of the first user may further include one of the following:

the controller sending the alarm information and video data captured by the video capturing sensor in the second state to a client of the second user; or, the controller displaying the alarm information on a display of a remote controller, and automatically displaying the video data captured by the video capturing sensor in the second state on the display of the remote controller or upon receiving a displaying request from the second user.

In a possible implementation, the remote controller is a controller at the side of the second user. In a possible implementation, the client may be a portable device of the second user, for example, a cellphone, a conventional laptop, or a wearable device such as smart glass or smart watch with communication functions and displaying functions. In a possible implementation, the client may be a vehicle-mounted device with communication functions and displaying functions.

As an optional or alternative implementation of displaying the alarm information on the display of the remote controller, the controller may display the alarm information on a display of the controller at the side of the first user, and automatically display video data captured by the video capturing sensor in the second state. In this implementation, the first user himself/herself can also be reminded of the abnormal physiological condition through the alarm information displayed and then take some self-help measures.

In another implementation, the second sensing device includes an audio detection sensor, and after generating the alarm information for notifying the second user of the physiological condition of the first user, the method for monitoring the physiological condition of the first user further includes:

the controller monitoring feedback information from the first user sent by the audio detection sensor; or when no feedback information is received from the first user, the controller performing at least one of the following operations:

triggering an awaking apparatus arranged at the first user; or, searching for an urgent contact user corresponding to the first user in a local database and sending notification information to a client of the urgent contact user.

In this implementation, the controller can monitor the feedback information sent by the audio detection sensor, and a determination is made whether feedback information is received by the controller from the first user. When the no feedback information is received by the controller from the first user, the controller may perform different operations.

As an optional or alternative implementation, the controller triggers the awaking apparatus arranged on the body of the first user. Specifically, when the no feedback information is received by the controller from the first user sent by the audio detection sensor, the controller can trigger the awaking apparatus arranged on the body of the first user. In a specific scenario, when no feedback information is received by the controller from the first user, it may be determined that the first user may fall asleep, and the controller can trigger the awaking apparatus arranged on the body of the first user to awake the first user, so that the second user can conduct a verbal communication with the first user. In a possible implementation, the awaking apparatus may be a buzzer, which can produce a buzzing sound as a signal. In a possible implementation, the awaking apparatus may be a tickler, which is capable of sending electrical stimulus to the first user, where the electrical stimulus is a safe current that can be applied to the human body without causing an alarm to the human body. The intensity of the electrical stimuli may be preset and adjustable, for example, the intensity of the electrical stimuli may be 5 mA direct current.

As another optional or alternative implementation, the controller may search for the urgent contact user corresponding to the first user in the local database and send the notification information to the client of the urgent contact user. Specifically, the local database may pre-store a list of the urgent contact user(s) corresponding to the first user, and the urgent contact user may be a relative and friend of the first user, which is not limited to the embodiments of the present disclosure. In a possible implementation, the notification information can be sent to the client of the urgent contact user in the form of a short message. In a possible implementation, the notification information can be notified to the urgent contact user by telephone.

In the embodiment of the present disclosure, the controller obtains the first sensing data of the first user reported by the at least one first sensing device, obtains the reference range corresponding to the first sensing data by taking at least one of an age, gender, medical condition and historical physiological condition of the first user, and a physiological parameter measured by the first sensing device into account, and determines the physiological condition of the first user based on the result derived from the first sensing data and the reference range corresponding to the first sensing data, and upon determining that the physiological condition of the first user is abnormal, sends the control instruction to the second sensing device to switch the second sensing device from the first state to the second state, through which, the physiological condition of the first user can be determined automatically and quickly, so that the second user (e.g., a doctor or caregiver) does not need to visit the first user frequently to determine the physiological condition of the first user, and thereby the cross-infection between the first user and the second user can be prevented; the reference range is determined taking many factors into account, so that the reference can be determined more reasonably according to personal conditions; in addition, the state of second sensing device can be controlled as required, thereby the greater flexibility for monitoring the physiological condition of the first user is provided.

In the above-described implementation, the reference range is obtained based on the baseline data, and those skilled in the art can understand that it is also possible to obtain the reference range in other ways, which will not be limited by the embodiments of the present disclosure. In addition, if there are many kinds of measurement data corresponding to different physiological parameters, there are also a plurality of reference ranges corresponding to the many kinds of measurement data respectively, where each kind of measurement data corresponds to a reference range. The present disclosure simply takes measurement data of respiratory rate as an example where the reference range related to respiratory rate is obtained based on the baseline data for the purpose of description, the calculation methods of various measurement data are similar to those of measurement data of respiratory rate as mentioned above.

It should be noted that the obtaining of the reference range is performed before step S202 or S302 of determining the physiological condition of the first user based on a result derived from the first sensing data and a reference range corresponding to the first sensing data. Other steps may be performed in a similar way as described in the above embodiments.

In a possible implementation, the controller may obtain the reference range from a trained reference range generation model. The reference range may be generated by the trained reference range generation model. The trained reference range generation model can be generated by training a neural network with physiological parameter data corresponding to the activities of the first user at respective time periods.

In a possible implementation, the controller may obtain the reference range according to a protocol, the protocol records the reference range corresponding to certain diseases.

In the above-mentioned embodiment, the reference range may be obtained in various manners. It should be noted that if there are many kinds of measurement data corresponding to different physiological parameters, there are also a plurality of reference ranges corresponding to the many kinds of measurement data respectively, and the reference ranges may be obtained by the methods mentioned above, where each kind of measurement data corresponds to a reference range.

Figure 6:
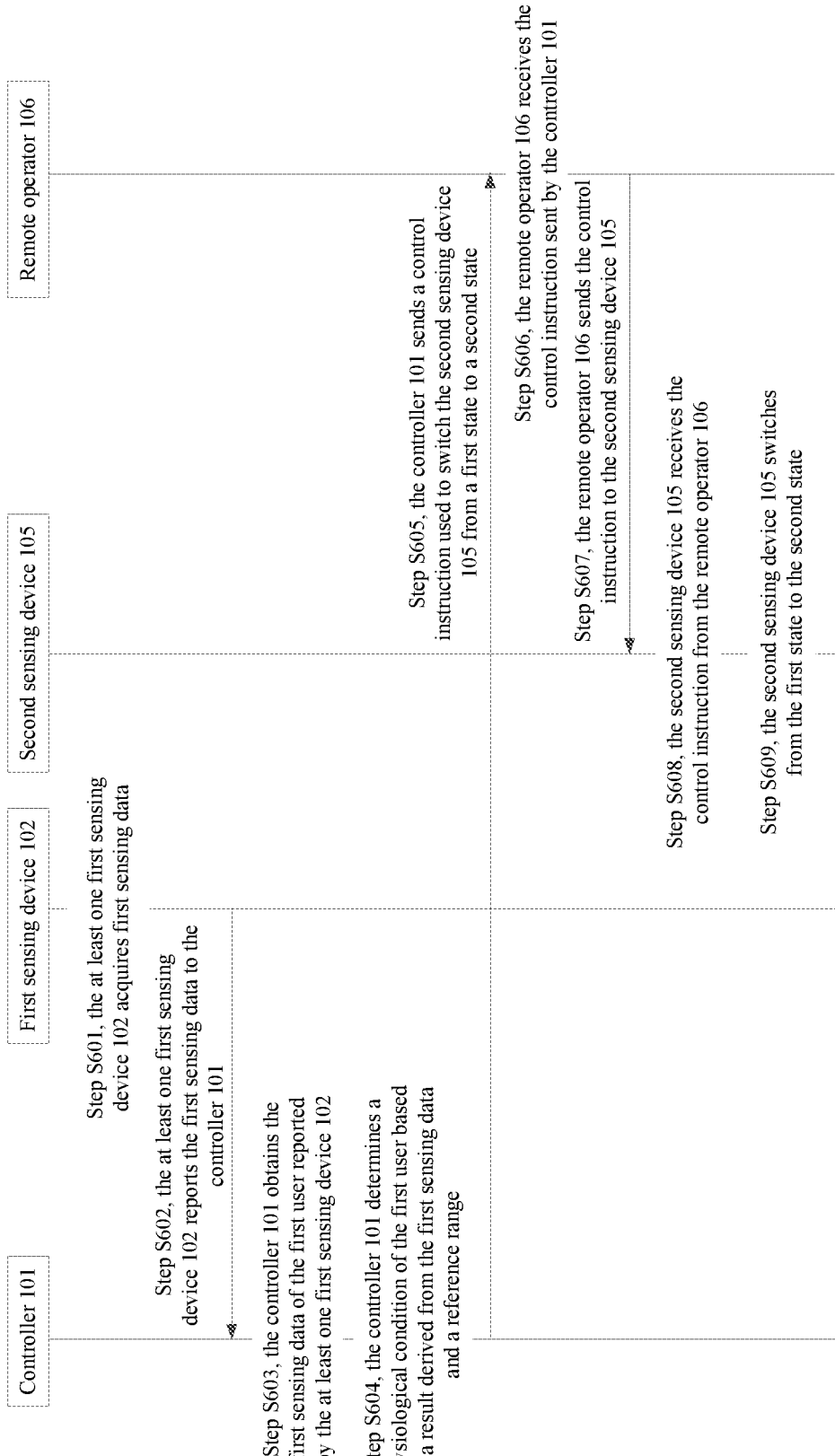
FIG. 6 is a schematic flowchart of a further method for monitoring a condition of a first user according to an embodiment of the present disclosure.

In order to describe the interaction between devices in system 100 of FIG. 1, FIG. 6 is provided, which is a schematic flowchart of a further method for monitoring a physiological condition of a first user according to an embodiment of the present disclosure. Specifically, the method may include the steps as follows.

The method includes the steps as described in the following. Some of the steps which have already been explained in the embodiment corresponding to FIG. 2 and FIG. 3 will not be elaborated again for conciseness. The method may be applied in the monitoring system shown in FIG. 1.

Step S601, the at least one first sensing device 102 acquires first sensing data.

Step S602, the at least one first sensing device 102 reports the first sensing data to the controller 101.

As described in step S301, the first sensing device 102 may include at least one of the following: a blood oxygen sensor, a breath rate sensor, a heart sensor.

Step S603, the controller 101 obtains the first sensing data of the first user reported by the at least one first sensing device 102.

Step S604, the controller 101 determines a physiological condition of the first user based on a result derived from the first sensing data and a reference range corresponding to the first sensing data.

Step S605, upon determining that the physiological condition of the first user is abnormal, the controller 101 sends a control instruction used to switch the second sensing device 105 from a first state to a second state.

In step S605, the control instruction is sent from the controller 101 to a remote operator 106, and the remote operator 106 is at the side of a second user and used by the second user (e.g., a doctor, a caregiver, or a relative or friend of the first user). In a possible implementation, the remote operator 106 is communicatively connected to the controller 101 and the second sensing device 105.

Step S606, the remote operator 106 receives the control instruction sent by the controller 101.

Step S607, the remote operator 106 sends the control instruction to the second sensing device 105.

Step S608, the second sensing device 105 receives the control instruction from the remote operator 106.

Step S609, the second sensing device 105 switches from the first state to the second state.

In a possible implementation, the second sensing device 105 includes a video sensing device and an audio sensing device. In a possible implementation, as mentioned in step S304, the system 100 further includes at least one data storage device communicatively connected to the controller 101 and the second sensing device 105; the at least one data storage device includes at least a long-term memory section and a short-term memory section; the controller 101 is capable of storing second sensing data from the second sensing device 105 selectively to the long-term memory section or the short-term memory section. In a possible implementation, the first state of the second sensing device 105 is a sleeping state or a short-term state, the second state of the second sensing device 105 is a long-term state, and the control instruction is further used to instruct the second sensing device 105 to store the second sensing data to the long-term memory section of the at least one data storage device. In a possible implementation, the short-term memory section is operating in a FIFO mode.

In a possible implementation, the second sensing device 105 and the at least one data storage device may be discrete devices, or the second sensing device 105 and the at least one data storage device may be integrated into one device.

Specifically, the short-term state of the second sensing device 105 refers to a working state that the second sensing device 105 stores the second sensing data to the short-term memory section of the data storage device, and the long-term state of the second sensing device 105 refers to another working state that the second sensing device 105 stores the second sensing data to the long-term memory section of the data storage device. The short-term memory section refers to a memory section that stores a small amount of information in a short period of time (e.g., one minute). The long-term memory section is a concept relative to the short-term memory section and refers to a memory section that stores information over a long period of time (e.g., a period of time more than one minute). The period of time that the short-term memory section or the long-term memory section can store data can be preset by the second user, which will not be limited by the embodiments of the present disclosure.

Figure 7:
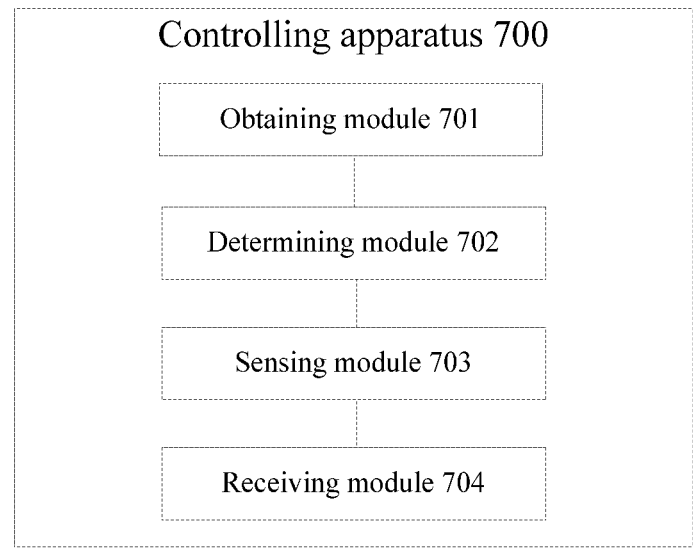
FIG. 7 is a schematic structural diagram of a controlling apparatus according to an embodiment of the present disclosure.

FIG. 7 is a schematic structural diagram of a controlling apparatus according to an embodiment of the present disclosure. As shown in FIG. 7, the controlling apparatus 700, which is communicatively connected to at least one first sensing device and a second sensing device, the second sensing device is capable of operating in a first state and a second state, and switching between the first state and the second state is controlled by the controlling apparatus 700; and the controlling apparatus 700 includes:

an obtaining module 701, configured to obtain first sensing data of a first user reported by the at least one first sensing device;

a determining module 702, configured to determine a physiological condition of the first user based on a result derived from the first sensing data and a reference range corresponding to the first sensing data, where the reference range is related to a physiological state of the first user; and a sensing module 703, configured to send a control instruction to the second sensing device to switch the second sensing device from the first state to the second state upon determining, by the determining module 702, that the physiological condition of the first user is abnormal.

In a possible implementation, the reference range is pre-set by a second user according to at least one of an age, gender, medical condition, and historical physiological condition of the first user, and a physiological parameter measured by the first sensing device.

In a possible implementation, the reference range is obtained as follows:

the determining module 702 is further configured to:
in response to detecting, by the obtaining module 701, that the first user is substantially in a peace state, determine the reference range according to a first setting; and
in response to detecting, by the obtaining module 701, that the first user is substantially in a moving state, determine the reference range according to a second setting.

In a possible implementation, the controlling apparatus 700 is further communicatively connected to at least one data storage device connected to the second sensing device; the at least one data storage device includes at least a long-term memory section and a short-term memory section; the controller is capable of storing second sensing data from the second sensing device selectively to the long-term memory section or the short-term memory section; the first state of the second sensing device is a sleeping state or a short-term state, the second state of the second sensing device is a long-term state, and the control instruction is further used to instruct the second sensing device to store the second sensing data to the long-term memory section of the at least one data storage device.

In a possible implementation, when the first state of the second sensing device is the short-term state, the control instruction is further used to copy the second sensing data of the second sensing device from the short-term memory section to the long-term memory section.

In a possible implementation, the at least one first sensing device includes a SpO2 sensor; the reference range of the first sensing data from the SpO2 sensor is between a first upper limit and a second lower limit pre-set by a second user; the first upper limit is within a range of 95-99%, and the second lower limit is within a range of 84-93%.

In a possible implementation, the at least one first sensing device includes a breath rate sensor, the reference range of the first sensing data from the breath rate sensor is between a third upper limit and a fourth lower limit; the third upper limit is selected by the second user between 20-25 beats per minute, and the fourth lower limit is selected by the second user between 9-15 beats per minute.

In a possible implementation, the at least one first sensing device includes at least one of the following: a SpO2 sensor, a breath rate sensor, a heart rate sensor, a respiratory muscle motion detection sensor, a cough detection sensor, a body movement sensor, and a lung sound detection sensor.

In a possible implementation, the second sensing device includes at least one of a video capturing sensor and an audio detection sensor.

In a possible implementation, the obtaining module 701 is further configured to:
perform preprocessing on the first sensing data to obtain the result derived from the first sensing data, where the preprocessing includes at least one of the following: data set selection, data compression, data filtering, and data cleaning.

In a possible implementation, the at least one first sensing device includes multiple first sensing devices configured for measuring a physiological parameter of the first user, and the determining module 702 is further configured to:
determine, among multiple temporary results derived from the first sensing data of the multiple first sensing devices, a number of temporary result derived from the first sensing data that is outside the reference range;
when the number is equal to zero, determine the physiological condition of the first user to be normal;
when the number is greater than zero, determine the physiological condition of the first user to be abnormal; and
upon determining that the physiological condition of the first user is abnormal, determine whether the number is greater than a first threshold;
the sensing module 703 is specifically configured to:
when the number is greater than zero, and smaller than or equal to the first threshold, send the control instruction to the second sensing device to switch the second sensing device from the first state to the second state;
when the number is greater than the first threshold, send the control instruction to the second sensing device to switch the second sensing device from the first state to the second state and generate alarm information for notifying a second user of the physiological condition of the first user.

In a possible implementation, where the controlling module includes a display module 704; the second sensing device includes a video capturing sensor, the sensing module 703 is further configured to:
send the alarm information and video data captured by the video capturing sensor in the second state to a client of the second user;
where the determining module 702 is further configured to:
control a remote controller to display the alarm information on a display of the remote controller, and control the remote controller to display the video data captured by the video capturing sensor in the second state the display of the remote controller automatically or upon receiving a displaying request from the second user.

In a possible implementation, the controller apparatus 700 further includes a receiving module 704, the second sensing device includes an audio detection sensor;
the receiving module 704 is further configured to:
monitor feedback information from the first user sent by the audio detection sensor;
the determining module 702 is further configured to:
when no feedback information is received from the first user, trigger an awaking apparatus arranged on a body of the first user; or, search for an urgent contact user corresponding to the first user in a local database and notify the sensing module 703 to send notification information to a client of the urgent contact user.

In a possible implementation, the at least one first sensing device includes multiple first sensing devices configured to measure physiological data of the first user, and
the determining module 702 is further configured to:
average the first sensing data reported by the multiple first sensing devices in a preset number of monitoring intervals; and
determine the physiological condition of the first user based on temporary results derived from the averaged first sensing data and the reference range corresponding to the first sensing data.

In a possible implementation, the determining module 702 is further configured to:
calculate a change rate of the result derived from the first sensing data;
determine whether the change rate is greater than a second threshold; and
when the result derived from the first sensing data falls within the reference range and the change rate is greater than the second threshold, determine that the physiological condition of the first user is abnormal.

In a possible implementation, the at least one first sensing device includes multiple first sensing devices configured to measure physiological data of the first user, and the determining module 702 is further configured to:
for each of the multiple first sensing devices, determine whether a temporary result derived from the first sensing data falls within the reference range;
count a first number of first sensing device, among the multiple first sensing devices, whose temporary result derived from the first sensing data falls within the reference range;
count a second number of first sensing device, among the multiple first sensing devices, whose temporary result derived from the first sensing data is outside the reference range; and
if the first number is equal to or greater than the second number, determine that the result derived from the first sensing data falls within the reference range.

In a possible implementation, the first sensing data includes at least one of the following: a respiratory rate, a heart rate, blood oxygen saturation, and sound data, where the sound data includes at least one of a duration, a frequency, and a sound amplitude of a coughing sound, a wheezing sound, a crackling sound, a rhonchi sound amplitude, and a whooping sound.

Figure 8:
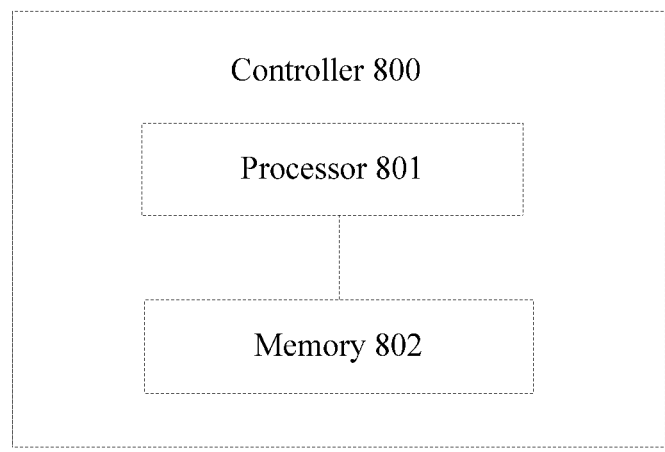
FIG. 8 is a schematic structural diagram of a controller according to an embodiment of the present disclosure.

FIG. 8 is a schematic structural diagram of a controller according to an embodiment of the present disclosure. As shown in FIG. 8, the controller 800 includes a processor 801 and a memory 802, where the processor 801 and the memory 802 are coupled to at least one first sensing device and a second sensing device; the second sensing device is capable of operating in a first state and a second state, and switching between the first state and the second state is controlled by the controller; and the memory 802 is configured to store therein computer instructions which, when executed by the processor 801, enable the processor 801 to:

obtain first sensing data of a first user reported by the at least one first sensing device; and determine a physiological condition of the first user based on a result derived from the first sensing data and a reference range corresponding to the first sensing data, where the reference range is related to a physiological state of the first user; and upon determining that the physiological condition of the first user is abnormal, send a control instruction to the second sensing device to switch the second sensing device from the first state to the second state.

In a possible implementation, the reference range is pre-set by a second user according to at least one of an age, gender, medical condition, and historical physiological condition of the first user, and a physiological parameter measured by the first sensing device.

In a possible implementation, the computer instructions which, when executed by the processor 801, enable the processor 801 to:

in response to detecting that the first user is substantially in a peace state, determine the reference range according to a first setting; and in response to detecting that the first user is substantially in a moving state, determine the reference range according to a second setting.

In a possible implementation, the controller is further communicatively connected to at least one data storage device connected to the second sensing device; the at least one data storage device includes at least a long-term memory section and a short-term memory section; the controller is capable of storing second sensing data from the second sensing device selectively to the long-term memory section or the short-term memory section;

the first state of the second sensing device is a sleeping state or a short-term state, the second state of the second sensing device is a long-term state, and the control instruction is further used to instruct the second sensing device to store the second sensing data to the long-term memory section of the at least one data storage device.

In a possible implementation, when the first state of the second sensing device is the short-term state, the control instruction is further used to copy the second sensing data of the second sensing device from the short-term memory section to the long-term memory section.

In a possible implementation, the at least one first sensing device includes a SpO2 sensor;

the reference range of the first sensing data from the SpO2 sensor is between a first upper limit and a second lower limit pre-set by a second user;

the first upper limit is within a range of 95-99%, and the second lower limit is within a range of 84-93%.

In a possible implementation, the at least one first sensing device includes a breath rate sensor, the reference range of the first sensing data from the breath rate sensor is between a third upper limit and a fourth lower limit;

the third upper limit is selected by the second user between 20-25 beats per minute, and the fourth lower limit is selected by the second user between 9-15 beats per minute.

In a possible implementation, the at least one first sensing device includes at least one of the following: a SpO2 sensor, a breath rate sensor, a heart rate sensor, a respiratory muscle motion detection sensor, a cough detection sensor, a body movement sensor, and a lung sound detection sensor.

In a possible implementation, the second sensing device includes at least one of a video capturing sensor and an audio detection sensor.

In a possible implementation, the computer instructions which, when executed by the processor 801, enable the processor 801 to:

perform preprocessing on the first sensing data to obtain the result derived from the first sensing data, where the preprocessing includes at least one of the following: data set selection, data compression, data filtering, and data cleaning.

In a possible implementation, the computer instructions which, when executed by the processor 801, enable the processor 801 to:

determine, among multiple temporary results derived from the first sensing data of the multiple first sensing devices, a number of temporary result derived from the first sensing data that is outside the reference range;

when the number is equal to zero, determine the physiological condition of the first user to be normal;

when the number is greater than zero, determine the physiological condition of the first user to be abnormal;

upon determining that the physiological condition of the first user is abnormal, determine whether the number is greater than a first threshold;

when the number is greater than zero, and smaller than or equal to the first threshold, send the control instruction to the second sensing device to switch the second sensing device from the first state to the second state;

when the number is greater than the first threshold, send the control instruction to the second sensing device to switch the second sensing device from the first state to the second state and generate alarm information for notifying a second user of the physiological condition of the first user.

In a possible implementation, the second sensing device includes a video capturing sensor, and the computer instructions which, when executed by the processor 801, enable the processor 801 to:

send the alarm information and video data captured by the video capturing sensor in the second state to a client of the second user; or, control a remote controller to display the alarm information on a display of the remote controller, and control the remote controller to display the video data captured by the video capturing sensor in the second state the display of the remote controller automatically or upon receiving a displaying request from the second user.

In a possible implementation, the computer instructions which, when executed by the processor 801, enable the processor 801 to:

monitor feedback information from the first user sent by the audio detection sensor when no feedback information is received from the first user, trigger an awaking apparatus arranged on a body of the first user; or search for an urgent contact user corresponding to the first user in a local database and send notification information to a client of the urgent contact user.

In a possible implementation, the at least one first sensing device includes multiple first sensing devices configured to measure physiological data of the first user, and the computer instructions which, when executed by the processor 801, enable the processor 801 to:

average the first sensing data reported by the multiple first sensing devices in a preset number of monitoring intervals; and determine the physiological condition of the first user based on temporary results derived from the averaged first sensing data and the reference range corresponding to the first sensing data.

In a possible implementation, the computer instructions which, when executed by the processor 801, enable the processor 801 to:

calculate a change rate of the result derived from the first sensing data;

determine whether the change rate is greater than a second threshold; and when the result derived from the first sensing data falls within the reference range and the change rate is greater than the second threshold, determine that the physiological condition of the first user is abnormal.

In a possible implementation, the at least one first sensing device includes multiple first sensing devices configured to measure physiological data of the first user, and the computer instructions which, when executed by the processor 801, enable the processor 801 to:

for each of the multiple first sensing devices, determine whether a temporary result derived from the first sensing data falls within the reference range;

count a first number of first sensing device, among the multiple first sensing devices, whose temporary result derived from the first sensing data falls within the reference range;

count a second number of first sensing device, among the multiple first sensing devices, whose temporary result derived from the first sensing data is outside the reference range; and if the first number is equal to or greater than the second number, determine that the result derived from the first sensing data falls within the reference range.

In a possible implementation, the first sensing data includes at least one of the following: a respiratory rate, a heart rate, blood oxygen saturation, and sound data, where the sound data includes at least one of a duration, a frequency, and a sound amplitude of a coughing sound, a wheezing sound, a crackling sound, a rhonchi sound amplitude, and a whooping sound.

The present disclosure also provides a non-transitory computer-readable storage medium, which stores therein computer executable instructions which, when being executed by a processor, implement the method for monitoring a condition of a first user according to embodiments of the present disclosure.

Terms such as "first", "second" and the like in the specification and claims of the present disclosure as well as in the above drawings are intended to distinguish different objects, but not intended to define a particular order.

The term "a" or "an" is not intended to specify one or a single element, instead, it may be used to represent a plurality of elements where appropriate.

In one or more examples, the functions described may be implemented in hardware, software, firmware, or any combination thereof. For example, the functions may be implemented by one or more processors, such as one or more application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, the techniques could be fully implemented in one or more circuits or logic elements.

In the claims, the word "including" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate, preclude or suggest that a combination of these measures cannot be used to advantage.

The foregoing detailed description has been presented for purposes of illustration and description. It is not intended to be exhaustive or to limit the subject matter claimed herein to the precise form(s) disclosed. Many modifications and variations are possible in light of the above teachings. The described embodiments were chosen in order to best explain the principles of the disclosed technology and its practical application to thereby enable others skilled in the art to best utilize the technology in various embodiments and with various modifications as are suited to the particular use contemplated. Those embodiments with various modifications are within the range and scope of the following claims.

The invention claimed is:

1. A method for monitoring a physiological condition of a first user, wherein the method comprises:

obtaining, by a controller, first sensing data of the first user reported by at least one first sensing device;

determining, by the controller, the physiological condition of the first user based on a result derived from the first sensing data and a reference range corresponding to the first sensing data, wherein the reference range is related to a physiological state of the first user; and determining that the physiological condition of the first user is abnormal, subsequently sending, by the controller, a control instruction to a second sensing device to switch the second sensing device from a first state to a second state, wherein the control instruction is further used to instruct the second sensing device to store second sensing data from the second sensing device to a long-term memory section of at least one data storage device and instruct the second sensing device to copy the second sensing data of the second sensing device from a short-term memory section of the at least one data storage device to the long-term memory section, wherein the second sensing device comprises a video capturing sensor, the first state of the second sensing device is a short-term state, the second state of the second sensing device is a long-term state, and wherein the short-term state of the second sensing device is a working state that the second sensing device stores the second sensing data to the short-term memory section of the at least one data storage device, and the long-term state of the second sensing device is another working state that the second sensing device stores the second sensing data to the long-term memory section of the at least one data storage device.

2. The method according to claim 1, wherein the reference range is pre-set by a second user according to at least one of an age, gender, medical condition, and historical physiological condition of the first user, and a physiological parameter measured by the first sensing device.

3. The method according to claim 1, wherein the reference range is obtained as follows:

in response to detecting that the first user is substantially in a peace state, determining, by the controller, the reference range according to a first setting;

in response to detecting that the first user is substantially in a moving state, determining, by the controller, the reference range according to a second setting.

4. The method according to claim 1, wherein the at least one first sensing device comprises a blood oxygen (SpO2) sensor;
the reference range of the first sensing data from the SpO2 sensor is between a first upper limit and a second lower limit pre-set by a second user;
the first upper limit is within a range of 95-99%, and the second lower limit is within a range of 84-93%.

5. The method according to claim 1, wherein the at least one first sensing device comprises a breath rate sensor, the reference range of the first sensing data from the breath rate sensor is between a third upper limit and a fourth lower limit, the third upper limit is selected by a second user between 20-25 beats per minute, and the fourth lower limit is selected by the second user between 9-15 beats per minute.

6. The method according to claim 1, wherein the at least one first sensing device comprises at least one of the following:
a SpO2 sensor, a breath rate sensor, a heart rate sensor, a respiratory muscle motion detection sensor, a cough detection sensor, a body movement sensor, and a lung sound detection sensor.

7. The method according to claim 1, wherein the second sensing device further comprises an audio detection sensor.

8. The method according to claim 1, further comprising:
performing, by the controller, preprocessing on the first sensing data to obtain the result derived from the first sensing data, wherein the preprocessing comprises at least one of the following:
data set selection, data compression, data filtering, and data cleaning.

9. The method according to claim 1, wherein the at least one first sensing device comprises multiple first sensing devices configured for measuring physiological data of the first user, and the method further comprises:
determining, by the controller, among multiple temporary results derived from the first sensing data of the multiple first sensing devices, a number of temporary result derived from the first sensing data that is outside the reference range;
wherein the determining, by the controller, the physiological condition of the first user based on the result derived from the first sensing data and the reference range corresponding to the first sensing data comprises:
when the number is equal to zero, determining, by the controller, the physiological condition of the first user to be normal;
when the number is greater than zero, determining, by the controller, the physiological condition of the first user to be abnormal;
wherein the upon determining that the physiological condition of the first user is abnormal, sending, by the controller, the control instruction to the second sensing device to switch the second sensing device from the first state to the second state comprises:
upon determining that the physiological condition of the first user is abnormal, determining, by the controller, whether the number is greater than a first threshold;
when the number is smaller than or equal to the first threshold, sending, by the controller, the control instruction to the second sensing device to switch the second sensing device from the first state to the second state;
when the number is greater than the first threshold, sending, by the controller, the control instruction to the second sensing device to switch the second sensing device from the first state to the second state and generating alarm information for notifying a second user of the physiological condition of the first user.

10. The method according to claim 9, wherein, after generating the alarm information for notifying the second user of the physiological condition of the first user, the method further comprises one of the following:
sending, by the controller, the alarm information and video data captured by the video capturing sensor in the second state to a client of the second user; or,
displaying, by a remote controller, the alarm information on a display of the remote controller, and automatically displaying the video data captured by the video capturing sensor in the second state on the display of the remote controller or upon receiving a displaying request from the second user.

11. The method according to claim 9, wherein the second sensing device comprises an audio detection sensor, and after generating the alarm information for notifying the second user of the physiological condition of the first user, and the method further comprises:
monitoring, by the controller, feedback information from the first user sent by the audio detection sensor; and
when no feedback information is received from the first user, performing, by the controller, at least one of the following operations:
triggering an awaking apparatus arranged on a body of the first user; or,
searching for an urgent contact user corresponding to the first user in a local database and sending notification information to a client of the urgent contact user.

12. The method according to claim 1, wherein the at least one first sensing device comprises multiple first sensing devices configured to measure physiological data of the first user, and before determining, by the controller, the physiological condition of the first user based on the result derived from the first sensing data and the reference range corresponding to the first sensing data, and the method further comprises:
averaging, by the controller, the first sensing data reported by the multiple first sensing devices in a preset number of monitoring intervals;
wherein the determining, by the controller, the physiological condition of the first user based on the result derived from the first sensing data and the reference range corresponding to the first sensing data, the method further comprises:
determining, by the controller, the physiological condition of the first user based on temporary results derived from the averaged first sensing data and the reference range corresponding to the first sensing data.

13. The method according to claim 1, wherein the determining, by the controller, the physiological condition of the first user based on the result derived from the first sensing data and the reference range corresponding to the first sensing data comprises:
calculating, by the controller, a change rate of the result derived from the first sensing data;
determining, by the controller, whether the change rate is greater than a second threshold; and
when the result derived from the first sensing data falls within the reference range and the change rate is greater than the second threshold, determining, by the controller, that the physiological condition of the first user is abnormal.

14. The method according to claim 1, wherein the at least one first sensing device comprises multiple first sensing devices configured to measure physiological data of the first user; and the method further comprises:
for each of the multiple first sensing devices, determining, by the controller, whether a temporary result derived from the first sensing data falls within the reference range;
counting, by the controller, a first number of first sensing device, among the multiple first sensing devices, whose temporary result derived from the first sensing data falls within the reference range;
counting, by the controller, a second number of first sensing device, among the multiple first sensing devices, whose temporary result derived from the first sensing data is outside the reference range; and
if the first number is equal to or greater than the second number, determining, by the controller, that the result derived from the first sensing data falls within the reference range.

15. The method according to claim 1, wherein the first sensing data comprises at least one of the following:
a respiratory rate, a heart rate, blood oxygen saturation, and sound data; wherein the sound data comprises at least one of a duration, a frequency, and a sound amplitude of a coughing sound, a wheezing sound, a crackling sound, a rhonchi sound amplitude, and a whooping sound.

16. The method according to claim 1, further comprising:
upon determining that the physiological condition of the first user returns to normal, sending, by the controller, a second control instruction to the second sensing device to switch the second sensing device from the second state to the first state.

17. The method according to claim 1, further comprising:
switching, by the controller, the second sensing device from the first state to the second state upon the control instruction is authorized.

18. A respiratory system for monitoring a physiological condition of a first user, comprising a controller, at least one first sensing device, a second sensing device, and at least one data storage device, wherein the at least one data storage device comprises at least a long-term memory section and a short-term memory section, the controller is communicatively connected to the at least one first sensing device, the second sensing device and the at least one data storage device, the second sensing device is configured to operate in a first state or a second state, and the controller is configured to:
control switching between the first state and the second state; obtain first sensing data of the first user reported by the at least one first sensing device; and
determine the physiological condition of the first user based on a result derived from the first sensing data and a reference range corresponding to the first sensing data, wherein the reference range is related to a physiological state of the first user; and
upon determining that the physiological condition of the first user is abnormal, send a control instruction to switch the second sensing device from the first state to the second state, wherein the control instruction is further used to instruct the second sensing device to store second sensing data from the second sensing device to the long-term memory section and instruct the second sensing device to copy the second sensing data of the second sensing device from the short-term memory section to the long-term memory section, wherein the second sensing device comprises a video capturing sensor, the first state of the second sensing device is a short-term state, and the second state of the second sensing device is a long-term state, and wherein the short-term state of the second sensing device is a working state that the second sensing device stores the second sensing data to the short-term memory section of the at least one data storage device, and the long-term state of the second sensing device is another working state that the second sensing device stores the second sensing data to the long-term memory section of the at least one data storage device;
wherein the first sensing device is configured to:
acquire the first sensing data; and
report the first sensing data to the controller;
wherein the second sensing device is configured to:
acquire the second sensing data;
receive the control instruction;
switch from the first state to the second state; and
store the second sensing data to the long-term memory section and copy the second sensing data of the second sensing device from the short-term memory section to the long-term memory section.

19. The system according to claim 18, further comprising a remote operator, wherein the remote operator is communicatively connected to the controller and the second sensing device;
the remote operator is configured to:
receive the control instruction sent by the controller; and
send the control instruction to the second sensing device.

20. The system according to claim 18, wherein the first sensing device further comprises at least one of the following:
a blood oxygen sensor, a breath rate sensor, a heart sensor;
wherein the second sensing device further comprises an audio sensing device;
wherein the short-term memory section is operating in a First-In-First-Out (FIFO) mode.

* * * * *